United States Patent [19]

Fumagalli et al.

[11] 4,009,183

[45] Feb. 22, 1977

[54] PROCESS FOR THE PREPARATION OF ALKYLENE CARBONATES

[75] Inventors: Carlo Fumagalli, Sirone (Como); Giuseppe Caprara, Milan; Paolo Roffia, Mantova, all of Italy

[73] Assignee: Montedison Fibre S.p.A., Milan, Italy

[22] Filed: Sept. 30, 1975

[21] Appl. No.: 618,201

[30] Foreign Application Priority Data

Sept. 30, 1974 Italy .................................. 27870/74

[52] U.S. Cl. .......................................... 260/340.2
[51] Int. Cl.$^2$ .............. C07D 317/38; C07D 317/36
[58] Field of Search ................................ 260/340.2

[56] References Cited

UNITED STATES PATENTS

| | | | |
|---|---|---|---|
| 2,766,258 | 10/1956 | Malkemus | 260/340.2 |
| 3,548,012 | 12/1970 | Cornforth | 260/634 |

*Primary Examiner*—Norma S. Milestone
*Attorney, Agent, or Firm*—Morgan, Finnegan, Pine, Foley & Lee

[57] ABSTRACT

The present invention concerns a process for preparing of alkylene carbonates, and more particularly it relates to a process for the direct preparation of alkylene carbonates from olefines.

More particularly, the present invention relates to a direct process for the preparation of alkylene carbonates, characterized in that an olefine selected from the group consisting of linear olefines and cyclic olefins having from 2 to 15 carbon atoms is reacted in a liquid phase with carbon dioxide in the presence of a gas selected from the group of oxygen and air and in the presence of a catalytic system consisting of:

a. iodine in a form selected from the group consisting of elementary iodine, alkali metal iodides, alkaline earth metal iodides, iodides of a metal selected from the group consisting of groups IB, IIB, IIIA, IIIB, IVA, VA, VIIB, and VIII of the periodic table and iodohydrines of the olefine reactant, and of b. an oxygen conveyor selected from the group consisting of manganese dioxide, nitrites, nitrates, nitrogen oxides and a cobalt complex;

at a temperature between 30° and 120° C., and at a pressure between atmospheric pressure to 100 atmospheres, and at a pH value between 3 and 8.

7 Claims, No Drawings

500
PROCESS FOR THE PREPARATION OF ALKYLENE CARBONATES

BACKGROUND OF THE ART

Alkylene carbonates, in particular ethylene and propylene-carbonate, find useful applications both as solvents for organic polymers such as electrochemical solvents as well as chemical intermediates. A well-known use of alkylene carbonates is their use as reactants for the production of alkylene oxides by heating the carbonates in the presence of a suitable catalyst.

Processes for the preparation of alkylene carbonates are already known. One known method consists in reacting an epoxide with carbon dioxide at high temperatures in the presence of suitable catalysts (e.g.: alkaline or ammonium halides, Lewis acids and organic bases, hydroxylated compounds). Another known method is based on the reaction between adjacent glycols and phosgene. It is also known to prepare alkylene carbonates starting from chlorohydrins in the presence of alkaline carbonates or bicarbonates.

The above referred to prior art processes have, however, the drawback of requiring the use of expensive intermediates as starting materials.

The object of this invention is that of providing a method for the preparation of alkylene carbonates, that be simple and cheap.

GENERAL DESCRIPTION OF THE INVENTION

It has now been found that it is possible to prepare alkylene carbonates by directly reacting an olefine with carbon dioxide and oxygen, in the presence of a suitable catalytic system.

More particularly, it has been discovered that a simple and inexpensive method for the production of an alkylene carbonate can be obtained by reacting and olefine selected from the group consisting of linear olefines and cyclic olefines having from 2 to 15 carbon atoms in a liquid phase with carbon dioxide in the presence of a gas selected from the group of oxygen and air and in the presence of a catalytic system consisting of:
   a. iodine in a form selected from the group consisting of elementary iodine, alkali metal iodides, alkaline earth metal iodides, iodides of a metal selected from the group consisting of groups IB, IIB, IIIA, IIIB, IVA, VA, VIIB, and VIII of the periodic table and iodohydrines of the olefine reactant, and of
   b. an oxygen conveyor selected from the group consisting of manganese dioxide, nitrites, nitrates, nitrogen oxides and a cobalt complex;
at a temperature between 30° and 120° C., and at a pressure between atmospheric pressure to 100 atmospheres, and at a pH value between 3 and 8.

If elementary iodine is used as the iodine component of the catalyst, it is possible to use a cation of an alkaline or alkaline earthy metal or of a metal chosen from the above indicated groups of the Periodic System, or the cation coming from the reduction of the oxygen conveyor, such as Na from sodium nitrite or Mn$^{++}$ from manganese dioxide.

The process according to this invention may be carried out either in one or two stages, depending on the oxygen conveyor used. When $MnO_2$ is used as the oxygen conveyor, the process is preferably realized in two stages. In the first stage there occurs the formation of the alkylene carbonate. In the second stage there is carried out the re-oxidation $Mn^{II}$ to $Mn^{IV}$ by means of oxygen.

Between the first and the second stage the alkylene carbonate that is formed, is removed by extraction with a suitable solvent immixible with $H_2O$.

When an organic or inorganic nitrite or nitrate, nitrogen oxide or a cobalt complex is used as the oxygen conveyor, the process is carried out in one single stage.

As indicated earlier, olefines used in the process of this invention are cyclic or linear olefines having from 2 to 15 carbon atoms. Olefines suited for the purpose are: ethylene, propene, butenes, pentenes, hexenes, octenes, cyclohexene.

Particularly suited alkali metal or alkaline earth metal iodides are sodium iodide, potassium iodide, magnesium iodide and barium iodides.

Metals suitable for forming iodides are chosen out of the groups IB, IIB, IIIA and B, IVA, VA, VIIB, VIII of the Periodic System the preferred metal iodides being copper iodide, bismuth iodide, cerium iodide and palladium iodide.

Compounds suitable for being used as oxygen conveyors in the process according to this invention are: manganese dioxide; the inorganic nitrites or nitrates selected from the group consisting of the alkali metal or alkaline earth metal nitrites or nitrates; in particular sodium nitrite or nitrate; organic nitrites or nitrates chosen from amongst butyl nitrite or nitrate, amyl nitrite or nitrate; the nitrogen oxides chosen from amongst $N_2O$, NO, $NO_2$; the cobalt complexes chosen from amongst the complexes with polydentate ligands such as for instance acetylacetonate, bis-salicylaldehyde-imino cobalt (II), etc.

Solvents useful for forming the reaction medium, are water or mixtures of water with polar solvents mixable with water. Solvents for admixture with water for forming the aforementioned solvent mixtures are: acetonitrile, dioxane, propyleneglycolcarbonate, alkyleneglycolcarbonates in general, alcohols; etc.

The water/solvent ratio may vary between 10:1 and 1:10, but is preferably comprised between 5:1 and 1:5.

The process according to this invention is conducted at temperatures comprised between 30° and 120° C. It is also possible to operate at room temperature, but of course to the detriment of the reaction kinetics. The preferred temperature range is comprised between 60° and 100° C.

The pressure used in this process may vary within wide intervals comprised between atmospheric pressure and 100 atm. The preferred range is comprised between 20 and 50 atm.

In order to obtain good selectivity properties in the alkylene carbonate, the pH of the reaction mixture must not be too low. In general, it is operated at a pH value between 3 and 8, but preferably between 4 and 7.

The concentrations of the reactants and of the constituents of the catalytic system are not critical.

The olefin/carbon dioxide/oxygen ratios may be those required by the stoichiometry of the reaction, but they may also vary within rather wide intervals.

The partial pressure of the olefine, carbon dioxide, oxygen should be such so as not to give origin to an explosive mixture. Thus it seems advantageous to use a high partial pressure of $CO_2$. It is rather convenient to keep the iodide ion concentration in solution the lowest possible, thus it is useful to use a metal whose iodide be little soluble.

The concentration of the cation of the alkaline or alkaline earth metal or of the metal may vary from 0.01 to 1.5 g. ions.liter$^{-1}$, but preferably be comprised between 0.1 and 1 g. ions.liter$^{-1}$.

According to this invention into the autoclave are first introduced the components of the catalytic system, then the olefine. The reaction mixture is then heated up to the desired temperature and to it is then added $CO_2$ and oxygen under pressure. In the event that $MnO_2$ is used as the oxygen conveyor, the above-described procedure is followed except that the reaction is two-stage instead of one stage. In the event that $MnO_2$ is used as oxidizer the addition of oxygen is not always necessary. After the formation of the alkylene carbonate, the $Mn^{II}$ is reoxidized $Mn^{IV}$ by means of oxygen in a second stage.

The absorption starts as soon as the $CO_2$ is introduced and the initial pressure is maintained through subsequent inlets of $CO_2$ and $O_2$.

At almost completed absorption, the reaction mixture is cooled down and then discharged. Thereupon the solid phase is removed by filtering and the liquid phase, containing the desired product and the possible iodohydrine intermediate, is extracted with solvents. The intermediate iodohydrine may be used again as iodine source for a further processing cycle.

SPECIFIC DESCRIPTION OF THE INVENTION

This invention will now be illustrated in more detail by the following examples.

EXAMPLE 1

Into an enameled autoclave of 2.3 lt holding capacity, fitted with a stirrer, were introduced:
57 g. of $MnO_2$ (0.65 moles) freshly prepared
100 g. of NaJ (0.67 moles)
300 cc. of water
400 cc. of acetonitrile.
Thereupon there were introduced 82 g. of propylene (1.95 moles), and the whole mixture was then heated up to a temperature of 70° C. Finally there were introduced 20.5 atmosphere of $CO_2$.

The total starting pressure amounted to about 35 atm. The absorption started as soon as the $CO_2$ was introduced and the pressure was maintained at the original level by subsequent inlets of $CO_2$.

Whenever the absorption slows down excessively (i.e., after 20 hrs.) the reaction mixture is cooled down and discharged. Thereby was obtained a solid and a liquid phase.

After removal of the solid phase by filtering, the liquid phase was extracted by means of a solvent (ether). The extracted solution was then analyzed by gas-chromatography; the only reaction product that was individualized proved to be propylene carbonate in a quantity of 41 g. (0.4 moles) with an almost quantitative selectivity with respect to the propylene consumed.

The yield in propylene carbonate with reference to the reduced $MnO_2$ turned out to be 65%.

The remaining oxidizing power of the $MnO_2$ was found to be
as unconverted $MnO_2$ = 8%
as elementary $J_2$ = 17%
as gaseous oxygen = 10%

EXAMPLE 2

Into an enameled 2.3 lt autoclave, fitted with a stirrer, were introduced:

53 g. of CuI (0.28 moles)
14 g. of $NaNO_2$ (0.2 moles)
600 cc. of water
150 cc. of acetonitrile.

Thereupon 80 g. of propylene (1.9 moles) were introduced, the whole was heated up to a temperature of 70° C. and finally there were introduced 13 atmospheres of $CO_2$ and subsequently 6 atmospheres of $O_2$, until reaching a total starting pressure of about 35 atm.

The absorption starts immediately after the introduction of the oxygen and the pressure is maintained at the initial level by reintegrating the $CO_2$ and the oxygen in the ratio of 2:1.

After 3 hours running, the reaction mixture was cooled down and discharged; the solid phase was filtered, while the liquid phase was extracted with ether. The extract was analyzed by gas-chromatography. Thereby were obtained:

12.3 g. (0.12 moles) of propylene carbonate and 7.5 g. (0.04 moles) of propylene iodohydrine. The propylene iodohydrine was separated and re-used as a iodine source for another processing.

EXAMPLE 3

In an enameled 2.3 lt autoclave, fitted with a stirrer, there were introduced:
51 g. (0.27 moles) of CuI
10 g. of $MgCO_3 \cdot nH_2O$
24 cc. (0.2 moles) of butyl nitrite
500 cc. $H_2O$
250 cc. acetonitrile,
thereupon 81 g. of propylene (∼2 moles) were introduced and the whole was heated up to 70° C.; lastly there were introduced 13 atm. of $CO_2$ and subsequently 6 atm. of $O_2$, until obtaining a total starting pressure of about 35 atmospheres.

The absorption started immediately after the introduction of the oxygen and the pressure was maintained at the initial level by reintegrating with $CO_2$ and $O_2$ in a ratio of 2:1.

After 5 hours running, the reaction mixture was cooled down and discharged, the solids were filtered off and the liquid phase extracted with ether.

The extract was analyzed by gas-chromatography and there were found 13 g. (0.13 moles) of propylene carbonate and 1.8 g. (0.01 moles) of propylene iodohydrine.

EXAMPLE 4

Into an enameled 2.3 lt autoclave, fitted with a stirrer, were introduced:
48 g. (0.55 moles) of freshly prepared $MnO_2$
51 g. (0.27 moles) of CuI
20 g. (0.24 moles) of $NaHCO_3$
500 cc. of $H_2O$
250 cc. of propylene carbonate
thereupon were introduced 83 g. (∼2moles) of propylene, and the whole was then heated up to 70° C. Finally there were introduced 18 atm. of $CO_2$ until obtaining a total initial pressure of about 35 atm.

The absorption started immediately and the pressure was maintained constant by reintegrating the $CO_2$.

After 9 hours running the reaction mixture was cooled down and 50 cc. of the solution were drawn and extracted with ether. On the etheral extract, was carried out a quantitative determination of the products formed, by a gas-chromatographic analysis and there were found:

41 g. (0.4 moles) of propylene carbonate and
7.3 g (0.034 moles) of propylene iodohydrine.

EXAMPLE 5

Into an enameled 2.3 lt autoclave, fitted with a stirrer, were introduced:
65 g. (0.75 moles) of freshly prepared $MnO_2$
40 g. (0.21 moles) of CuI
22 g. (0.26 moles) of $NaHCO_3$
500 cc. $H_2O$
250 cc. of acetonitrile,
thereupon were introduced 115 g. (2.05 moles) of butene-1. The whole wax then heated up to a temperature of 70° C. and at last were introduced 20 atmospheres of $CO_2$, until obtaining a total initial pressure of about 30 atm. The pressure was maintained constant by reintegrating the $CO_2$.

After 9 hours running, the reaction mixture was cooled down and discharged. the solid phase was filtered and the liquid phase was extracted with ether. The ethereal extract was analyzed by gas-chromatography and there were found 30 g. (0.26 moles) of butylene carbonate.

EXAMPLE 6

Into an enameled 2.3 lt autoclave, fitted with a stirrer, were introduced:
70 g. (0.8 moles) of freshly prepared $MnO_2$
85 g. (0.33 moles) of $I_2$
300 cc. of $H_2O$
400 cc. acetonitrile.
Thereupon there were introduced 80 g. (1.9 moles) of propylene and the whole was then heated up to 70° C.; finally there were introduced 24 atmospheres of $CO_2$. The initial pressure amounted to about 35 atmospheres.

The absorption started immediately after introduction of $CO_2$, and the pressure was maintained at the initial value by successive inlets of $CO_2$.

Whenever the absorption slows down excessively (i.e., after 8 hrs.) the reaction mixture is cooled down and discharged; the solids are filtered and the liquid phase is extracted with ether.

The etheral extract was analyzed by gas-chromatography; the following substances were obtained:
42 g. (0.42 moles) of propylene carbonate
73.3 g. (0.40 moles) of propylene iodohydrine.

We claim:
1. Process for the direct preparation of alkylene carbonates, characterized in that cyclic olefines, linear olefines and having from 2 to 15 carbon atoms is made to react in a liquid phase with carbon dioxide in the presence of a catalytic system consisting of:
   a. iodine in a form selected from the group consisting of elementary iodine, alkali metal iodides, alkaline earth metal iodides, iodides of a metal selected from the group consisting of group IB, IIB, IIIA, IIIB, IVA, VA, VIIB, and VIII of the periodic table and iodohydrines of the olefine reactant, and of
   b. an oxygen conveyor consisting of manganese dioxide;
at temperatures comprised between 30° and 120° C., and at pressures comprised between atmospheric pressure and 100 atm., at a pH value comprised between 3 and 8.

2. Process according to claim 1, characterized in that the iodine is in a form selected from the group consisting of sodium iodide, potassium iodide, magnesium iodide and barium iodide.

3. Process according to claim 1, characterized in that the iodine is in a form selected from the group consisting of Copper iodide, Bismuth iodide, Cerium iodide and Palladium iodide.

4. Process according to claim 1, characterized in that the temperature is between 60° and 100° C., and the pressure is between 20 and 50 atm. at the pH value of between 4 and 7.

5. Process according to claim 1, characterized in that the olefines used in the process is selected from the group consisting of ethylene, propene, butenes, pentenes, hexenes, octenes and cyclohexene.

6. Process according to claim 1, wherein the iodine is in the form of sodium iodide.

7. Process according to claim 1, wherein the iodine is in the form of copper iodide.

* * * * *

UNITED STATES PATENT AND TRADEMARK OFFICE
CERTIFICATE OF CORRECTION

PATENT NO. : 4,009,183
DATED : February 22, 1977
INVENTOR(S) : Carlo Fumagalli, Giuseppe Caprara and Paolo Roffia It is certified that error appears in the above-identified patent and that said Letters Patent are hereby corrected as shown below:

On page 1, the Assignee should be --Montedison S.p.A.-- instead of "Montedison Fibre S.p.A."

In claim 1, line 2, after "that" insert --an olefin selected from the group consisting of--.

Column 1, line 38, change "and" to --an--.

In claim 5, column 6, line 36, change "olefins" to --olefin--.

Signed and Sealed this sixteenth Day of August 1977

[SEAL]

Attest:

RUTH C. MASON
*Attesting Officer*

C. MARSHALL DANN
*Commissioner of Patents and Trademarks*